United States Patent [19]

Mitchell

[11] Patent Number: 5,292,705
[45] Date of Patent: Mar. 8, 1994

[54] ACTIVATION OF HYDROCARBON SYNTHESIS CATALYST

[75] Inventor: Willard N. Mitchell, Baton Rouge, La.

[73] Assignee: Exxon Research & Engineering Co., Florham Park, N.J.

[21] Appl. No.: 949,935

[22] Filed: Sep. 24, 1992

[51] Int. Cl.$^5$ .................. B01J 21/06; B01J 23/74; B01J 23/96; C07C 1/04
[52] U.S. Cl. .................. 502/325; 518/700; 518/715; 502/260; 502/332
[58] Field of Search .................. 502/325, 332

[56] References Cited

U.S. PATENT DOCUMENTS 3,792,110  2/1974  Senn, III et al. .................. 502/30

FOREIGN PATENT DOCUMENTS 2222531A  3/1990  United Kingdom .......... B01J 23/90

OTHER PUBLICATIONS

Vannice, M. A., The Catalytic Synthesis of Hydrocarbons from $H_2$/CO Mixtures over the Group VIII Metals, J. of Catalysis 37, 449–461 (1975).

Vannice, M.A., Titania-Supported Metals as CO Hydrogenation Catalysts, Journal of Catalysis 74, 199–202 (1982).

Catalysis, vol. IV, Hydrocarbon Synthesis, Hydrogenation and Cyclization, ed by Paul H. Emmett, Reinhold Publishing, New York (1961) pp. 105–108.

*Primary Examiner*—Paul E. Konopka
*Attorney, Agent, or Firm*—Jay Simon

[57] ABSTRACT

A fresh, reduced hydrocarbon synthesis catalyst is activated by contact with hydrogen at elevated temperatures and pressures and in the presence of liquid hydrocarbons, preferably, sufficient to immerse the catalyst therein.

10 Claims, 1 Drawing Sheet

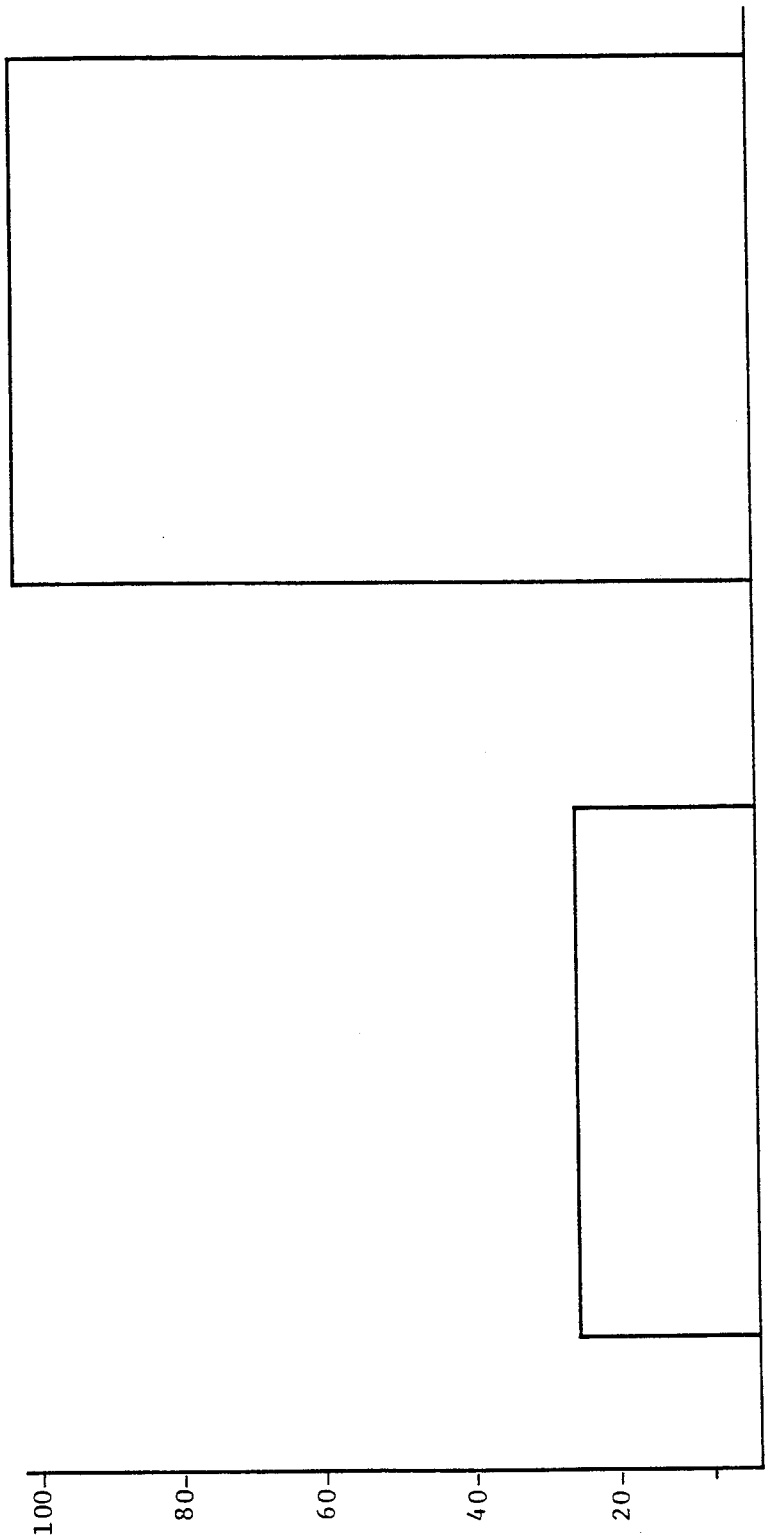

ACTIVATION OF HYDROCARBON SYNTHESIS CATALYST

FIELD OF THE INVENTION

This invention relates to activating a hydrocarbon synthesis catalyst. More particularly, the activating step comprises treating a reduced, essentially fresh, hydrocarbon synthesis catalyst with hydrogen in the presence of hydrocarbon containing liquids.

BACKGROUND OF THE INVENTION

Hydrocarbon synthesis catalysts come in a variety of types, perhaps, the most useful being supported catalysts where the catalytic metal may be a Group VIII metal, e.g., Fe, Co, Ru, and the support is any relatively inert material known in the art as a catalyst support, e.g., difficulty reducible inorganic refractory oxides or kielseguhr, diatomeaceous earths, etc. The catalytic metal can be incorporated into the support in many different ways, e.g., kneading, impregnation, spraying, etc. Nevertheless, regardless of the method of preparation, the final activating step is usually a treatment with hydrogen or a hydrogen containing gas. This final activating step, whether a first or second or subsequent hydrogen treating step, is usually performed ex situ, but can be performed in the reactor just prior to start up, particularly for fixed bed units.

SUMMARY OF THE INVENTION

In accordance with this invention, the activity of a hydrocarbon synthesis catalyst may be enhanced by treating the reduced hydrogen treated, essentially fresh, i.e., unused, catalyst with hydrogen in the presence of hydrocarbon containing liquids, preferably slurry liquids that can be subsequently used in slurry phase hydrocarbon synthesis, e.g., as in a bubble column slurry reactor. The "super" activation treatment is effected in the presence of sufficient liquid for fully immersing the catalyst and at elevated temperatures and pressures, preferably at about synthesis reaction pressures, and temperatures of no more than about 100° F. ($\sim$40° C.) below synthesis reaction temperatures. The "super" activation treatment may be performed in situ, particularly for subsequent slurry phase hydrocarbon synthesis reactions or in a separate treatment vessel. Preferably, hydrogen in the absence of CO, and free of oxygen is injected into a slurry of hydrocarbons and the catalyst, preferably with sufficient energy from the hydrogen alone, to disperse the catalyst particles in the liquid. The hydrogen can be neat or mixed with inerts such as $N_2$, $CO_2$, or $CH_4$, preferably nitrogen.

While the mechanism for this "super" activation is not well understood, it may be that additional metal in the surface layer is reduced, or that deposits are removed from the metal surface, or both, but in any event more metal is available for catalysis.

Usually, on a relative activity scale, catalyst activity or productivity may be substantially increased, that is, by at least about thirty percent (30%) more preferably by at least about fifty percent (50%), and still more preferably by at least about seventy-five percent (75%) by the method of this invention. While catalyst activity can be increased whether the catalyst is subsequently employed in fixed bed or slurry phase operation, the latter is a preferred mode of operation. Further, the active catalytic material can be any of the Group VIII metals, particularly however, iron, cobalt or ruthenium, cobalt being particularly preferred.

The increase in catalyst productivity obtained by this invention by virtue of the slurry phase hydrogen treatment is relative to the productivity that would have been obtained had there been no additional hydrogen treatment. Additionally, this super activation method encompasses hydrogen treatment both before introduction of synthesis gas into the reactor at hydrocarbon synthesis reaction conditions and hydrogen treatment shortly after the synthesis reaction has begun, i.e., at no later than a 10% reduction in productivity, not more than a 5% reduction in relative catalyst productivity.

BRIEF DESCRIPTION OF THE DRAWING

FIG. 1 shows, in bar graph form, catalyst activity on the ordinate as represented by relative productivity (where productivity is volumetric productivity and equals volume CO converted/hour/volume of catalyst), before and after the super activation treatment with hydrogen, the catalyst being in a hydrocarbon liquid slurry.

DETAILED DESCRIPTION OF THE INVENTION

Hydrocarbon synthesis processes particularly those for producing $C_5+$ hydrocarbons, are usually carried out at elevated temperatures and pressures typical of Fischer-Tropsch processing. Thus, pressures may range from 1–100 atmospheres, preferably 5–40 atmospheres, more preferably 10–25 atmospheres. Temperatures may range from about 175° C. to 450° C., preferably 175° C.–425° C., most preferably 175° C. to 300° C., and hydrogen to carbon monoxide ratios in the feed gas may range from about 1.5 to 4.0, preferably about 1.7 to 2.5.

In slurry phase operations, the slurry usually contains about 10 to 50 wt% catalyst solids, preferably 30 wt% to 40 wt% solids. The catalyst is normally maintained in suspension, that is, dispersed, in the slurry liquid, by a combination of product recycle liquid, slurry recycle liquid, recycle product gas, and injected feed gas. Preferably, the feed gas provides the majority of energy, more preferably essentially all of the energy, for maintaining the catalyst dispersion.

For ease of operation, particularly slurry phase operation, the super activation technique can be effected at hydrocarbon synthesis reaction conditions, whatever they may be, but preferably at elevated temperatures and pressures. Typically, the temperature may range to about 100° F. below synthesis reaction conditions while pressures are maintained at or about reaction conditions. Hydrogen treat rates during the super activation typically range from about 10–50 SCF/lb catalyst, preferably about 15–30 SCF/lb catalyst; or on another basis, from about 599–5000, preferably 1500–3000 SCF/lb hydrocarbons. The hydrogen may be introduced as hydrogen or as a hydrogen containing gas, e.g., hydrogen and nitrogen. The period necessary for activation is that period that results in a substantial increase in initial, e.g., start of run, catalyst productivity, preferably at least about a thirty percent (30%) increase in relative catalyst productivity and may vary with temperature and treat ratio, etc., but is usually accomplished in about 0.25-24 hours, preferably about 0.5-2 hours.

The hydrogen may be plant or refinery hydrogen and is used as received. In this condition, it is substantially free of water, that is, less than about 0.5 wt% water in the hydrogen. However, in one embodiment of this invention, the activation is effected by hydrogen in the presence of water, e.g., 0.5-25 wt%, added to the hydrogen or hydrogen containing activation gas stream. The water may also be added to the slurry hydrocarbons.

Perhaps, the reason slurry phase super activation was not previously attempted is due to the widespread belief that hydrogen treatment at elevated temperatures and pressures of hydrocarbons in the presence of a hydrogenation catalyst (i.e., Fischer-Tropsch synthesis can be viewed as the hydrogenation of CO) would lead to hydrogenolysis of the liquids resulting in methane formation, the most unwanted product in Fischer-Tropsch synthesis, and coke formation that would deleteriously affect catalyst life and activity. However, because of the relatively short treatment time, coke does not form and hydrogenolysis is virtually non-existent. As a consequence, hydrogen treatment in the presence of liquid hydrocarbons should be continued only for so long as necessary to obtain maximum activity enhancement but should not be continued for relatively longer periods of time, i.e., those which will lead to hydrogenolysis of the liquids or coke formation or both.

The hydrocarbon liquids used for immersing the catalyst during the activation are those that are liquid at hydrocarbon synthesis reaction conditions, generally inert, and a good solvent for synthesis gas. Typically, the slurry is the product of the reaction and contains $C_{5+}$ hydrocarbons, usually $C_5$-$C_{50}$ hydrocarbons. However, the slurry liquid comprises primarily high boiling paraffins, with small amounts of olefins, primary and secondary alcohols, acids, esters, or mixtures thereof. The high boiling paraffins include primarily $C_{10}$-$C_{50}$ linear hydrocarbons. The slurry liquid can contain hetero oxygen atoms, but sulfur, nitrogen, phosphorus, arsenic, or antimony atoms are to be avoided since these act as poisons for the hydrocarbon synthesis process. Examples of specific slurry materials are: dodecane, tetradecane, hexadecane, octadecane, hexatriacontaine, tetracosane, octacosane, and the like. Preferred slurry materials are Fischer-Tropsch waxes, and $C_{16}$-$C_{18}$ alkyl hydrocarbons.

The catalyst is preferably a supported catalyst wherein the support is preferably a difficulty reducible inorganic oxide of Groups III, IV, V, VI and VIII of the Periodic Chart of the Elements. Particularly preferred supports are the Group IVB oxides, especially those having a surface area of 100 m$^2$/gm or less, preferably 70 m$^2$/gm or less. A particularly preferred support contains primarily rutile titania.

The catalyst metal is a Group VIII metal, preferably cobalt, iron or ruthenium more preferably cobalt, or ruthenium, and most preferably cobalt, and is present in catalytically active amounts, usually about 1-50 wt%, preferably 2-40 wt%, more preferably about 2-25 wt%. Promoters may be added to the catalyst and are well known in the Fischer-Tropsch catalyst art. Promoters can be ruthenium (when it is not the primary catalytic metal), rhenium, hafnium, cerium, and zirconium, and are usually present in amounts less than the primary catalytic metal (except for ruthenium which may be present in co-equal amounts). However, the promoter:metal ratio should at least be about 1:10; rhenium and hafnium being preferred promoters.

Catalyst preparation may be accomplished by a variety of techniques, although catalyst preparation does not play a part in this invention and the hydrogen treatment disclosed herein will improve the activity of the hydrocarbon synthesis catalyst however it is prepared.

A typical catalyst preparation may involve impregnation, by incipient wetness or other known techniques of, e.g., a cobalt nitrate salt onto a titania, silica, or alumina support, optionally followed or proceeded by impregnation with a promoter material, e.g., perrhenic acid. Excess liquid is removed and the catalyst precursor dried at 100° C. to 125° C. Following drying or as a continuation thereof, the catalyst is calcined at about 300° C.-500° C. to convert the salt or compound to its corresponding oxide(s). The oxide is then reduced by treatment with hydrogen or a hydrogen containing gas at about 300° C.-500° C. for a period of time sufficient to substantially reduce the oxide to the elemental or catalytic form of the metal. Some prefer an additional cycle of oxidation/reduction. Another, and sometimes preferred method for catalyst preparation is disclosed in U.S. Pat. No. 4,621,072 incorporated herein by reference. Nevertheless, the catalyst subjected to the slurry phase hydrogen treatment of this invention is one that has already been reduced by conventional means. Thus, the catalyst has, essentially, not been previously used in hydrocarbon synthesis.

EXAMPLES

In a hydrocarbon synthesis process demonstration unit, hydrogen treatment of the catalyst to enhance initial activity for slurry phase operations was demonstrated. In the unit, fresh catalyst 12 wt% Co, 1 wt% Re on a titania support with 6 wt% $Al_3O_3$ as a binder material, was activated by first reducing the catalyst in hydrogen to reduce the cobalt oxide to the cobalt metal. This was accomplished in a fluid bed reactor at temperatures up to about 375° C.. The $H_2$ treat gas rate was 8-18 SCFH $H_2$/lb catalyst with a $H_2$ concentration of 18-25% in $N_2$. Following the reduction the catalyst was passivated with 0.25-1.3 SCFH of CO in $N_2+H_2$ for 1-2 hours.

The dry reduced catalyst was combined with wax to form a slurry in a slurry mix vessel. The slurry was transferred to the hydrocarbon synthesis reactor and synthesis was initiated. Following a short test to measure initial catalyst productivity, a hydrogen treat was conducted in the slurry reactor ("super" activation). The following table shows two examples of this "super" activation:

|  | Relative Productivity | |
| --- | --- | --- |
|  | Before | After |
| Example 1 | 60 | 100 |
| Example 2 | 25 | 100 |

In the first example the relative productivity increased from 40% to 100% and in the second case from 25% to 100%. The conditions for the $H_2$ treat of the slurry were typical of conditions described earlier.

In order to determine the real increase in initial activity, the catalyst had to be run at synthesis conditions for a period sufficient to obtain an initial activity or productivity. However, this minimal operation at synthesis conditions is not believed to change or effect the catalyst in any substantive way and the catalyst may be considered as essentially fresh catalyst.

What is claimed is:

1. A method for activating an essentially fresh, reduced cobalt containing Fischer-Tropsch catalyst which comprises treating the catalyst with hydrogen or a hydrogen containing gas in the presence of hydrocarbon liquids for a period sufficient to increase substantially the initial catalyst productivity.

2. The method of claim 1 wherein activation is effected at temperatures ranging from 135° C.–425° C.

3. The method of claim 1 wherein the catalyst is dispersed in the hydrocarbon liquids.

4. The method of claim 3 wherein at least a portion of the energy required for maintaining the catalyst in a dispersion is supplied by injection of hydrogen or hydrogen containing gas.

5. The method of claim 3 wherein activation is effected at elevated temperatures and pressures.

6. The method of claim 5 wherein the pressure is about hydrocarbon synthesis pressure and the temperature ranges from hydrocarbon synthesis temperature to no more than about 40° C. below hydrocarbon synthesis temperature.

7. The method of claim 5 wherein initial catalyst productivity is increased by at least about 30%.

8. The process of claim 3 wherein the hydrocarbon liquids are Fischer-Tropsch slurry liquids.

9. The method of claim 1 wherein the catalyst is supported.

10. The method of claim 9 wherein the support is a Group IVB oxide.

* * * * *